United States Patent [19]
Maeda et al.

[11] Patent Number: 5,589,899
[45] Date of Patent: Dec. 31, 1996

[54] OPTHALMOLOGIC APPARATUS HAVING A SLIDABLE BED

[75] Inventors: Yasuo Maeda, Kawasaki; Kyoji Sekiguchi, Yokohama, both of Japan

[73] Assignee: Canon Kabushiki Kaisha, Tokyo, Japan

[21] Appl. No.: 361,044

[22] Filed: Dec. 21, 1994

[30] Foreign Application Priority Data

Dec. 22, 1993 [JP] Japan .................. 5-324577

[51] Int. Cl.$^6$ .................. A61B 3/00; A61B 3/14
[52] U.S. Cl. .................. 351/245; 351/208
[58] Field of Search .................. 351/200, 205, 351/206, 208, 212, 245

[56] References Cited

U.S. PATENT DOCUMENTS

| | | | |
|---|---|---|---|
| 4,572,627 | 2/1986 | Madate et al. | 351/206 |
| 4,660,946 | 4/1987 | Nakamura et al. | 351/212 |
| 4,666,269 | 5/1987 | Nakamura et al. | 351/212 |
| 4,690,525 | 9/1987 | Kobayashi et al. | 351/206 |
| 4,697,895 | 10/1987 | Sekiguchi et al. | 351/243 |
| 4,710,003 | 12/1987 | Masuda et al. | 351/212 |
| 4,762,410 | 8/1988 | Sekiguchi et al. | 351/206 |
| 4,878,750 | 11/1989 | Sekiguchi | 351/212 |
| 5,056,522 | 10/1991 | Matsumura et al. | 351/212 |
| 5,116,114 | 5/1992 | Nakamura et al. | 351/205 |
| 5,302,979 | 4/1994 | Maeda et al. | 351/212 |

FOREIGN PATENT DOCUMENTS

| | | |
|---|---|---|
| 2-265525 | 10/1990 | Japan . |
| 2-279130 | 11/1990 | Japan . |

*Primary Examiner*—Huy Mai
*Attorney, Agent, or Firm*—Fitzpatrick, Cella, Harper & Scinto

[57] ABSTRACT

An ophthalmologic apparatus having a slidable bed slidable horizontally and vertically to observe, measure, and photograph an eye to be examined. The ophthalmologic apparatus has a base, a slidable bed slidable on the base, a joy stick for permitting a user to control sliding of the slidable bed, a monitor for effecting image display, and a control unit for controlling a displayed image on the monitor in response to the operation of the joy stick.

13 Claims, 11 Drawing Sheets

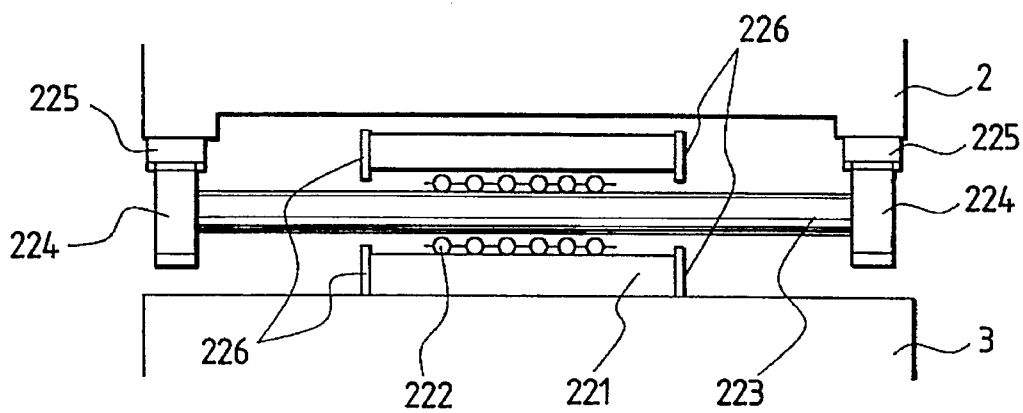
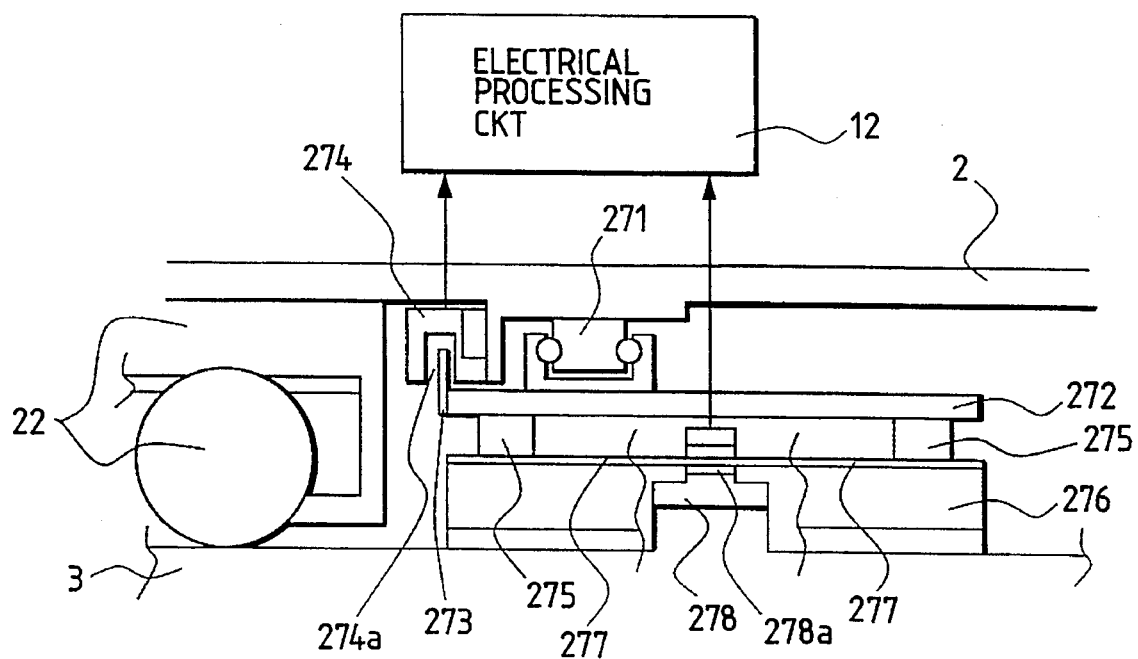

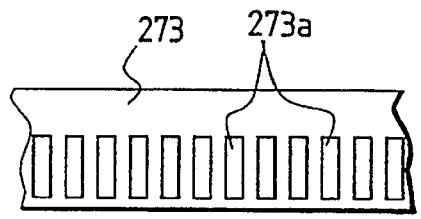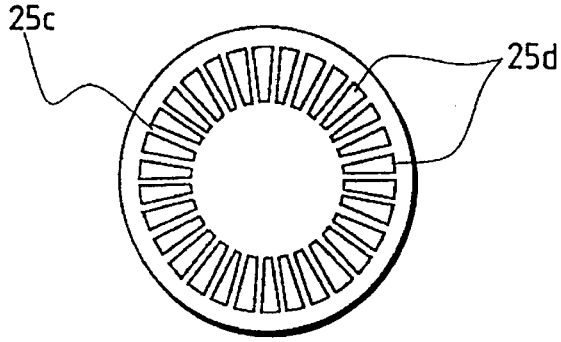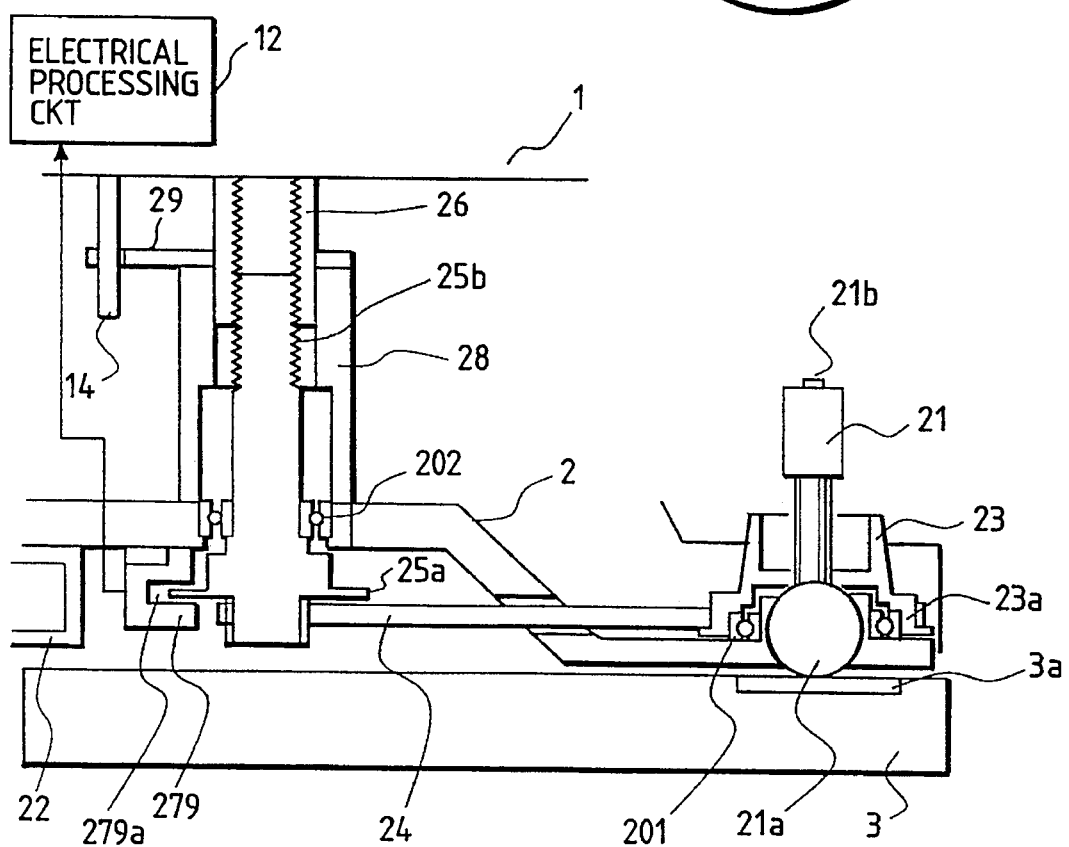

Ep

D=2.0

Ep   4b

OPTHALMOLOGIC APPARATUS HAVING A SLIDABLE BED

BACKGROUND OF THE INVENTION

1. Field of the Invention

This invention relates to an ophthalmologic apparatus having a slidable bed horizontally and vertically slidable to observe, measure and photograph an eye to be examined.

2. Related Background Art

In an ophthamologic apparatus according to the prior art, a slidable bed carrying thereon an image pickup unit for picking up the image of and measuring and eye to be examined is horizontally slid on an immovable base and this image pickup unit is vertically moved to thereby effect the alignment of the eye to be examined and the image pickup and measurement of the eye to be examined are effected by the image pickup unit. When in such an apparatus, the details of the picked-up image are to be observed, a switch for inputting, vertically and horizontally provided discretely from a switch used for measurement, etc., is operated when an image stored in a frame memory is displayed on a monitor, and further a region to be observed in detail on an enlarged scale is displayed on the monitor.

Such an apparatus, however, suffers from the disadvantage that the construction of the switches is complicated and the operation thereof is cumbersome to an examiner.

SUMMARY OF THE INVENTION

In view of the above-noted disadvantage peculiar to the prior art, it is an object of the present invention to provide an ophthalmologic apparatus in which switches are simplified and the simplification of operation is realized.

Other objects of the present invention will become apparent from the following detailed description of some embodiments of the invention.

BRIEF DESCRIPTION OF THE DRAWINGS

FIG. 2 partially shows the construction of the same apparatus.

FIG. 3 partially shows the construction of the some apparatus.

FIG. 4 is an illustration of a slit plate

FIG. 5 partially shows the construction of the apparatus according to the first embodiment.

FIG. 6 is an illustration of a slit plate.

DESCRIPTION OF THE PREFERRED EMBODIMENTS

Figure 1:
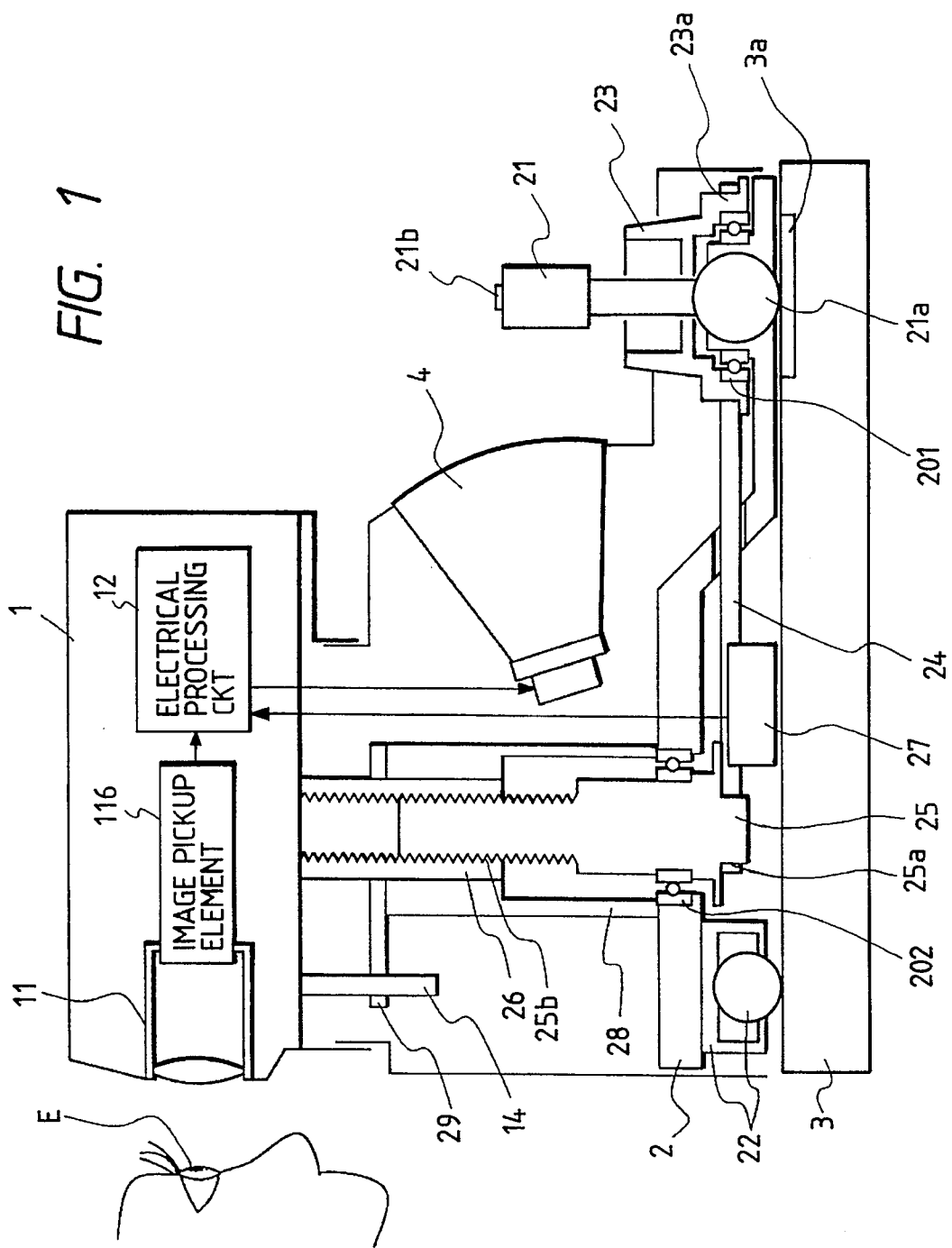
FIG. 1 illustrates the general construction of an ophthalmologic apparatus according to a first embodiment of the present invention.

FIG. 1 illustrates the construction of an ophthalmologic apparatus according to a first embodiment of the present invention, and FIG. 2 partially shows the construction of the same apparatus. This embodiment is one in which the present invention is applied to an ophthalmologic apparatus for observing and photographing the turbidity of the intermediate light-transmitting bodies (crystalline lens and vitreous body) of an eye E to be examined or observing and photographing the image of the front eye part of the eye E to be examined and measuring the diameter of the pupil thereof and the diameter of the cornea thereof. The construction and operation of the present embodiment will hereinafter be described.

The reference numeral 1 designates an image pickup unit, the reference numeral 2 denotes a slidable bed, the reference numeral 3 designates a base, the reference character 3a denotes a slide plate, the reference numeral 4 designates a monitor, the reference numeral 12 denotes an electrical processing circuit including an image control unit, the reference numeral 14 designates a detent shaft, the reference numeral 21 denotes a joy stick, the reference character 21a designates a joy stick ball, the reference numeral 22 denotes a sliding guide member, the reference numeral 23 designates a vertically movable ring, the reference characters 23a and 25a denote timing pulley portions, the reference numeral 24 designates a timing belt, the reference numeral 25 denotes a vertically movable drive shaft, the reference character 25b designates a drive screw portion, the reference numeral 26 denotes a vertically movable strut, the reference numeral 27 designates a movement amount detecting unit, the reference numeral 28 denotes a strut, the reference numeral 29 designates a detent plate, the reference numerals 201 and 202 denote bearings for the rotation of the vertically movable ring 23 and the vertically movable drive shaft 25, respectively, the reference numeral 221 designates a guide tube, the reference numeral 222 denotes a bearing, the reference numeral 223 designates a horizontally movable shaft, the reference numeral 224 denotes a pinion, the reference numeral 225 designates a guide rack, and the reference numeral 226 denotes a stopper.

An examiner operates the joy stick 21 to thereby slide the slidable bed 2 carrying the image pickup unit 1 thereon on the base 3 horizontally relative to the eye E to be examined, and rotates the vertically movable ring 23 to thereby move the image pickup unit 1 vertically and effect the alignment of the eye E to be examined.

The forward and backward movement and rightward and leftward movement of the slidable bed 2 are effected by inclining the joy stick 21 to thereby roll the joy stick ball 21a on the slide plate 3a provided on the base 3, and pushing or pulling the joy stick 21 to thereby slide the joy stick ball 21a on the slide plate 3a.

The sliding guide member 22 provided on that side of the slidable bed 2 which is adjacent to the eye to be examined operates as a guide for the rightward and leftward movement of the slidable bed 2 by a construction in which the horizontally movable shaft 223 moves in the guide tube 221 mounted on the base 3 through the bearing 222, as shown in FIG. 2. Also, the pinion 224 attached to the end surface of the horizontally movable shaft 223 is adapted to mesh with the guide rack 225 attached to the slidable bed 2 and operate as a guide for the forward and backward movement of the slidable bed 2. The stopper 226 prevents the falling off of the bearing 222.

Also, the vertical movement of the image pickup unit 1 is effected as follows. When the vertically movable ring 23 is rotated, the rotation of the vertically movable ring 23 is transmitted to the vertically movable drive shaft 25 having the timing pulley portion 25a meshing with the timing pulley portion 23a formed on a portion of the vertically movable ring 23 through the timing belt 24 meshing with the timing pulley portion 23a, whereby the vertically movable drive shaft 25 is rotated. Further, by the rotation of the vertically movable drive shaft 25, the vertically movable strut 26 meshing with the drive screw portion 25b formed on a portion of the vertically movable drive shaft 25 is vertically moved and the image pickup unit 1 fixed to one end of the vertically movable strut 26 is vertically moved.

The amount of forward and backward movement and the amount of rightward and leftward movement of the slidable bed 2 slid forwardly and backwardly and rightwardly and leftwardly as described above and the amount of vertical movement of the image pickup unit 1 may be detected by the electrical processing circuit 12 which will be described later.

The strut 28 is secured as the guide portion of the vertically movable strut 26 to the slidable bed 2, and by the fitting of the detent plate 29 secured to the end surface of the strut 28, as shown, to the detent shaft 14 secured to the image pickup unit 1, the image pickup unit 1 is prevented from being rotated by the rotation of the vertically movable drive shaft 25.

FIG. 3 shows as example of the construction of the movement amount detecting unit 27 shown in FIG. 1, and is a detailed view of a mechanism provided near the sliding guide member 22 for detecting the amount of forward and backward movement and the amount of rightward and leftward movement of the slidable bed 2.

One side of a rightward and leftward movement guide member 271 is fixed to the slidable bed 2 and the other side thereof is fixed to a plate 272, and the design Of the design is such that with the rightward and leftward movement of the slidable bed 2, the plate 272 moves relative to the slidable bed 2 in a direction perpendicular to the plane of the drawing sheet of FIG. 3. A slit plate 273 having openings 273a provided at equal intervals as shown in FIG. 4 is attached to one end of the plate 272, and the design of the device is such that by the movement of the plate 272 in the direction perpendicular to the plane of the drawing sheet resulting from the aforedescribed rightward and leftward movement of the slidable bed 2, a number of openings 273a in the slit plate 273 proportional to the amount of movement pass through the gap 274a of a photoencoder 274 secured to the slidable bed 2. The photoencoder 274 is designed to detect the number and direction of those of the openings 273a which have passed through the gap 274a to thereby detect the amount and direction of rightward and leftward movement of the slidable bed 2 at any time. The construction of this photoencoder is well known and therefore need not be described herein.

Also, the amount and direction of forward and backward movement of the slidable bed 2 guided by a forward and backward movement guide member 276 having one side thereof secured to the plate 272 through a connecting member 275 and the other side thereof secured to the base 3 are likewise detected. That is, the design of the devices is such that the number and direction of those of openings in a slit plate 277 secured to the plate 272 through the connecting member 275 and having openings similar to the openings 273a in the slit plate 273 which move through a gap 278a with the forward and backward movement of the slidable bed 2 are detected by a photoencoder 278 fixed to the base 3.

FIG. 5 is a detailed view of the mechanism portion of the movement amount detecting unit 27 for detecting the amount of vertical movement of the image pickup unit 1. This detecting mechanism detects the amount and direction of rotation of the vertically movable drive shaft 25 to thereby detect the amount of vertical movement. That is, a photoencoder 279 is secured to the slidable bed 2 so that a slit portion 25c attached to a portion of the vertically movable drive shaft 25 and having openings 25d disposed at equal intervals as shown in FIG. 6 may move through the gap 279a of the photoencoder 279. The photoencoder 279 is designed to detect the number and direction of those of the openings 25d which have passed through the gap 279a to thereby detect the amount and direction of rotation of the vertically movable drive shaft 25 and detect the amount and direction of vertical movement of the image pickup unit 1 at any time.

The above-described means for detecting the amount and direction of forward and backward movement and rightward and leftward movement of the slidable bed 2 and the amount and direction of vertical movement of the image pickup unit 1 are not limited to photoencoders, but may be other means such as rotary encoders, potentiometers or magnetic detectors (magnescales). Also, the mechanism by which the detecting means detects the respective amounts of movement may be replaced by a mechanism as described in Japanese Laid-Open Patent Application No. 2-265525 or Japanese Laid-Open Patent Application No. 2-279130.

Figure 7:
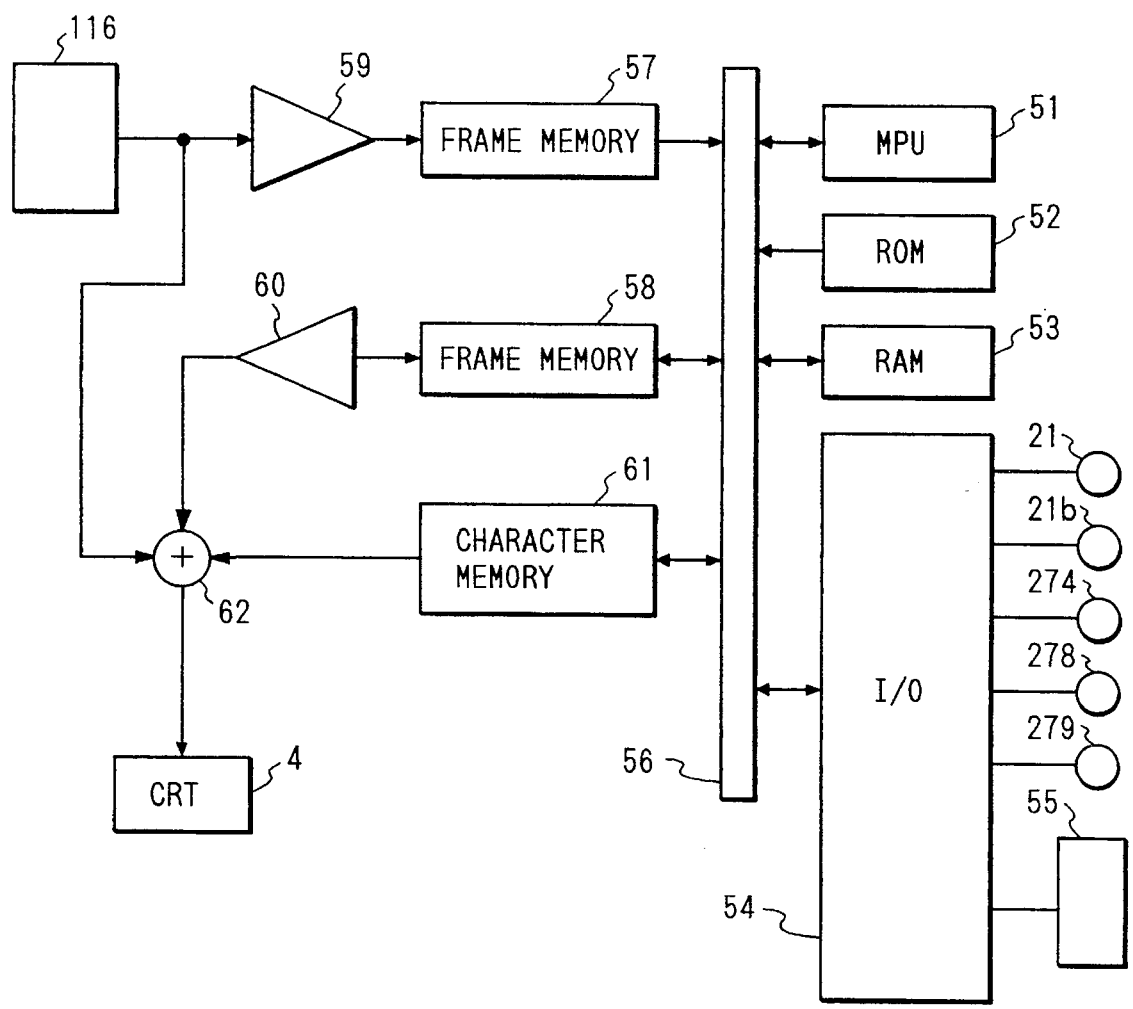
FIG. 7 illustrates the construction of the circuit portion of the apparatus according to the first embodiment.

FIG. 7 is a block diagram of the electrical processing circuit 12. The reference numeral 51 designates a microprocessor, the reference numeral 52 denotes a ROM in which is written a program for controlling the present apparatus, and the reference numeral 53 designates a RAM. The reference numeral 54 denotes an i/o interface to which are connected the joy stick 21, the measuring switch 21b, the photoencoders 274, 278, 279 and an interface connector 55 for connection to a floppy disc, a magneto-optical disc or the like. The reference numeral 56 designates a control bus for a microcomputer system to which are connected an A/D converter 59 for converting a video signal from an image pickup element 116 such as a CCD into a digital signal, a frame memory 57 for storing the digitally converted image therein, a frame memory 58 for displaying the image on the CRT(4), and a character memory 61 for displaying characters such as the result of measurement and graphics such as cursors on the CRT(4). The digital image data from the frame memory 58 is converted into an analog signal by a D/A converter 60, and the character signal from the character memory 61 and the video signal from the image pickup element 116 are superposed one upon the other or and changed over by a mixing circuit 62 and the output video signal thereof is displayed on the CRT(4).

The CRT(4) is also controllable so as to directly display the video signal from the image pickup element 116, or to transfer the image stored in the frame memory 57 to the frame memory 58 and display it, or enlarge and process a part of it, or to display characters alone, as shown in FIGS. 8 to 21.

Figure 22:
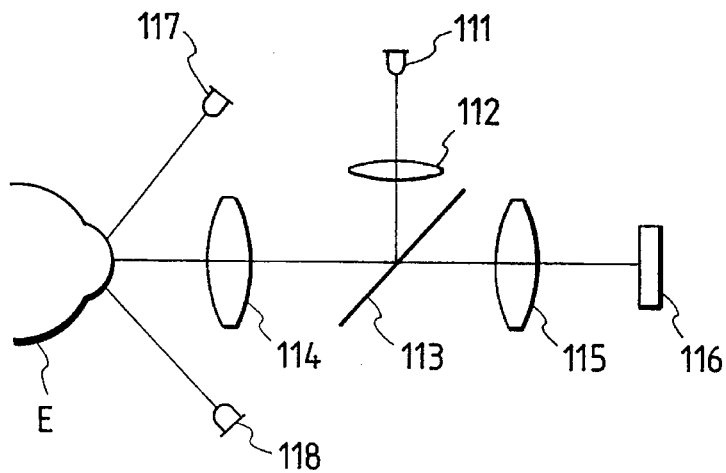
FIG. 22 partially shows the construction of the optical system portion of the apparatus according to the first embodiment.

FIG. 22 illustrates an example of the optical arrangement of the image pickup optical system 11. A beam of light from a light source 111 which illuminates the interior of the eye E to be examined is transmitted through a relay lens 112, is reflected by a half mirror 113 and arrives at the fundus of the eye E to be examined through an objective lens 114. This beam of light illuminating the fundus of the eye is further reflected by the fundus of the eye and emerges out of the eye from the pupil of the eye E to be examined as if the fundus of the eye became an illuminating light source.

The design of the device is such that if at this time, an image pickup element 116 such as a CCD is aligned with a desired position, in the eye E to be examined, of the imaging beam of light transmitted through the objective lens 114, the half mirror 113 and an imaging lens 115 and imaged, for example, on a position conjugate with a cloud in the vitreous body or a cloud in the crystalline lens, the image of that region will be obtained. Light sources 117 and 118 are light sources for illuminating the front eye part of the eye E to be examined.

Figure 8:
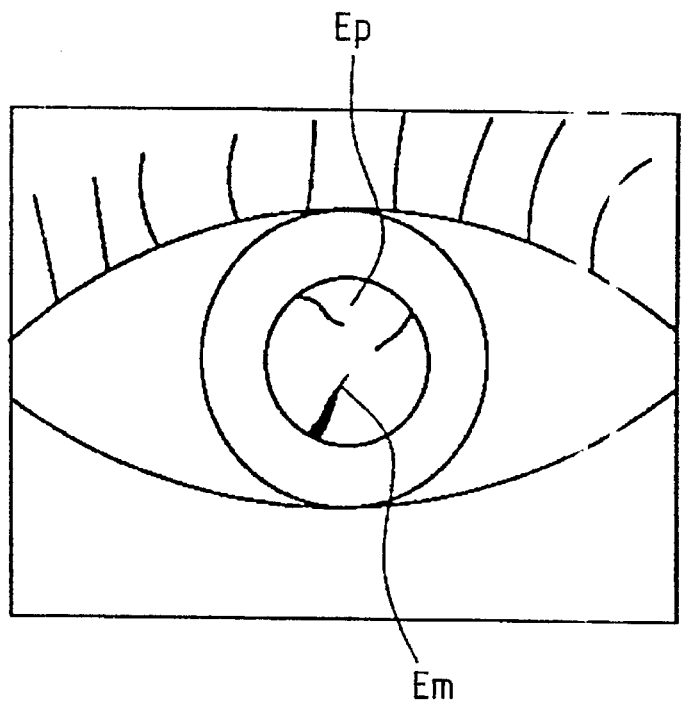
FIG. 8 illustrates the monitor display in the apparatus according to the first embodiment.

FIG. 8 shows the image of the front eye part of the eye E to be examined on the monitor obtained by the above-described construction and operation, and more particularly shows the image when the optical system is focused on a cloud in the crystalline lens of the eye E to be examined. In FIG. 8, Ep designates the pupil of the eye E to be examined, and Em denotes a cloud in the crystalline lens. A description will hereinafter be provided of the operation of the device when a part of the introduced image is enlarged.

Figure 9:
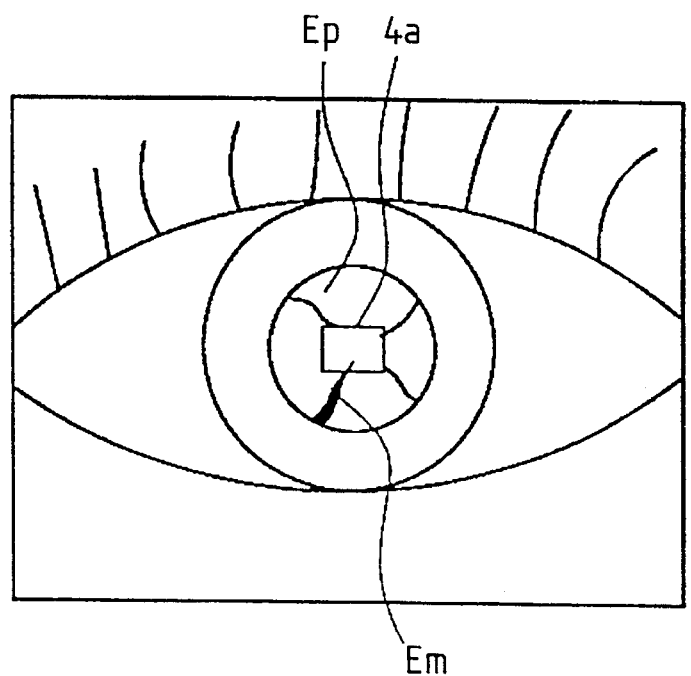
FIG. 9 illustrates the monitor display in the same apparatus.

The examiner first effects predetermined alignment with the eye to be examined, and thereafter depresses a measuring switch 21b. Thereby, the operation of the joy stick 21 is changed over to input means for image processing as will be described below. By the depression of the measuring switch 21b, the image on the monitor 4 shown in FIG. 8 is first stored in the frame memory 57. The image stored in the frame memory 57 is then transferred to the frame memory 58, whereafter it is again called up and is displayed on the monitor 4. This image is shown in FIG. 9. The image shown in FIG. 9 is always of the same magnification as the image shown in FIG. 8 and therefore, when the more detailed enlarged image of the cloud Em in the crystalline lens is to be obtained, the examiner operates the joy stick 21 to thereby move the slidable bed 2 forwardly and backwardly and rightwardly and leftwardly so that the region to be enlarged may come into a frame 4a indicating the enlarged range displayed on the monitor. The amount and direction of this movement are detected by the encoders 274 and 278, respectively, and the movement of the image in an amount and direction corresponding to the result of this detection is effected on the monitor 4. That is, in conformity with the result of the detection, image processing for moving the stored image is carried out with the frame 4a being kept fixed on the monitor 4.

Figure 10:
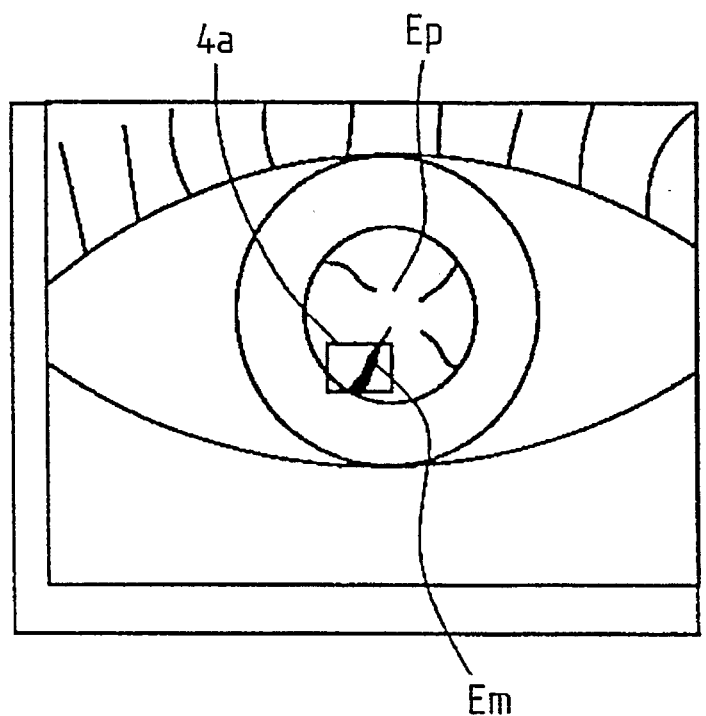
FIG. 10 illustrates the monitor display in the same apparatus.
Figure 11:
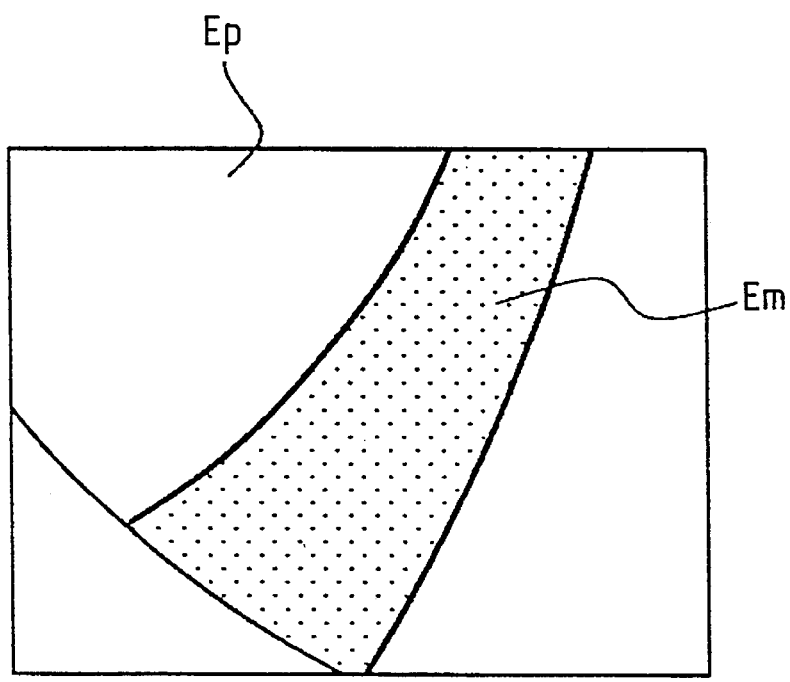
FIG. 11 illustrates the monitor display in an ophthalmologic apparatus according to another embodiment of the present invention.

In this manner, the image is moved so that the predetermined image region to be enlarged may come into the frame 4a as shown in FIG. 10, whereafter the measuring switch 21b is depressed, whereupon that image portion is enlarged and displayed on the monitor 4 as shown in FIG. 11. When the examiner thereafter depresses the measuring switch 21b, the image on the monitor restores the state shown in FIG. 9.

The enlargement magnification is determined by the size of the frame 4a. The size of the frame 4a is variable by rotating the vertically movable ring 23.

Figure 12:
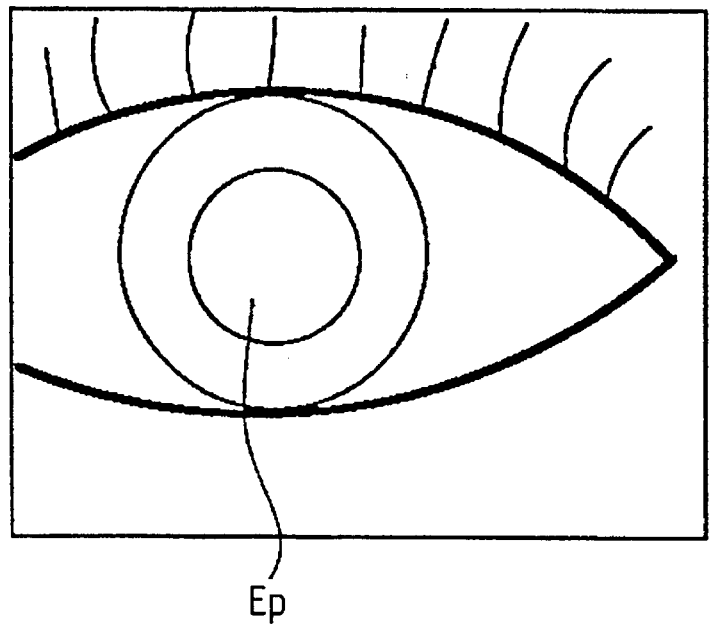
FIG. 12 illustrates the monitor display in the same apparatus.
Figure 13:
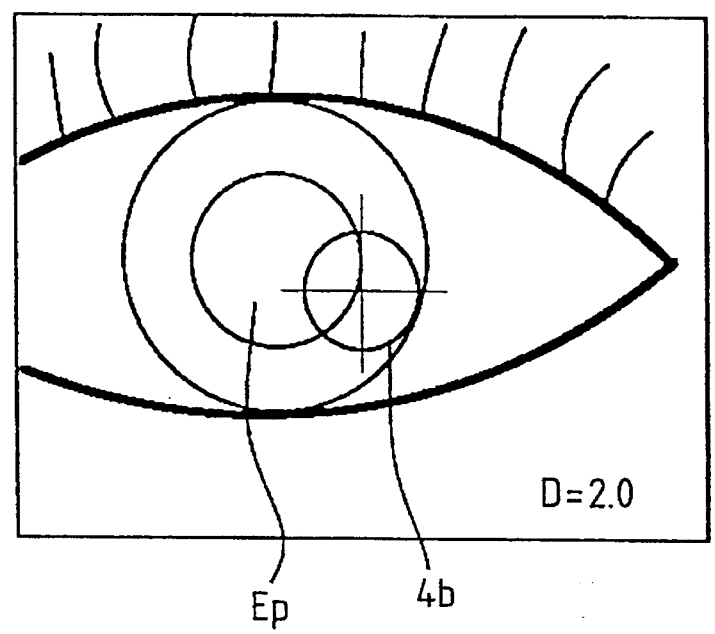
FIG. 13 illustrates the monitor display in the same apparatus.
Figure 14:
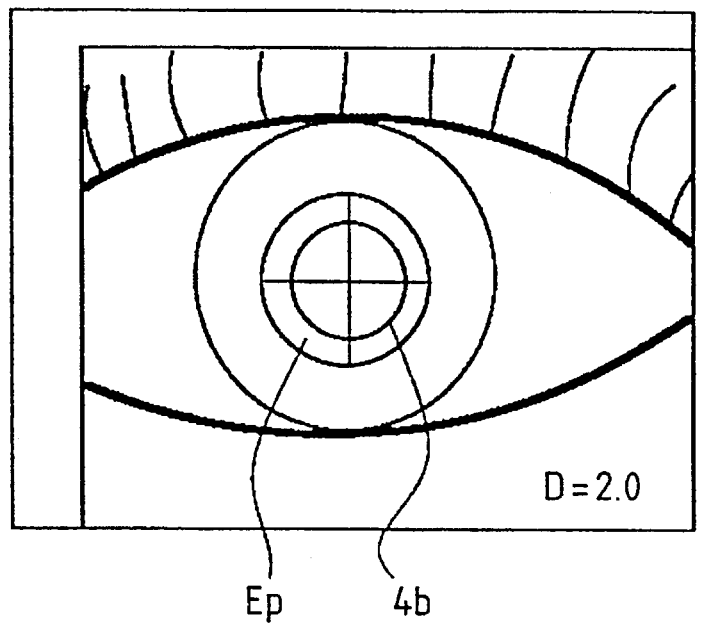
FIG. 14 illustrates the monitor display in the same apparatus.
Figure 15:
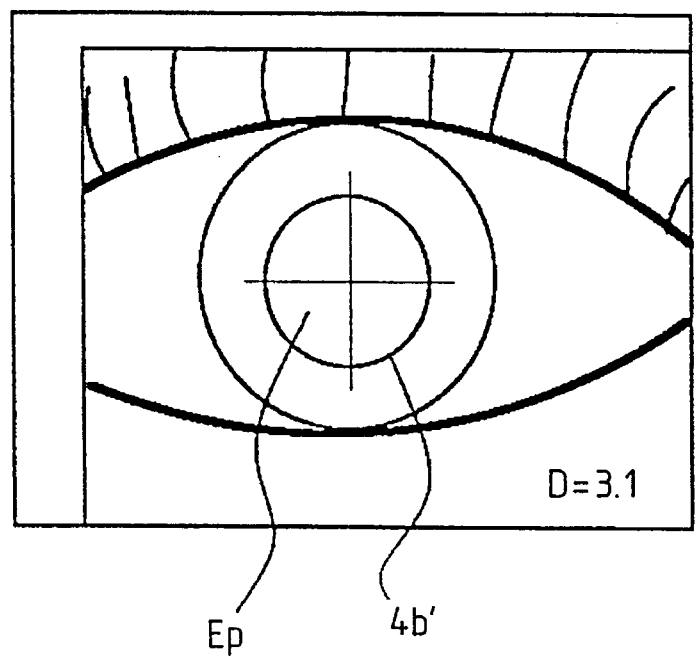
FIG. 15 illustrates the monitor display in the same apparatus.

A case where the present apparatus is an apparatus having the function of measuring the diameter of the pupil will now be described as another embodiment of the present invention. Alignment is effected so that the pupil portion of the eye to be examined may be displayed on the monitor 4 as shown in FIG. 12, and after the completion of the alignment, the measuring switch 21b is depressed, whereupon the displayed image is stored in the frame memory 57, and the image data is transferred to the frame memory 58 for display and is displayed on the monitor 4 as shown in FIG. 13. In FIG. 13, Ep designates the pupil, the reference character 4b denotes a mark for the measurement of the diameter of the pupil, and "D=2.0" displayed on the right lower portion of the monitor 4 indicates the (imaginary) diameter of the mark on the pupil corresponding to the current diameter of the mark 4b on the monitor. When from this state, the joy stick 21 is moved forwardly and backwardly and rightwardly and leftwardly, and the image of the eye to be examined moves on the monitor as previously described. By the operation of the joy stick, the mark 4b and the pupil are made coaxial on the monitor as shown in FIG. 14. When in this state, the vertically movable ring 23 is rotated, the amount and direction of the rotation thereof are detected by the encoder 279 and image processing is carried out so that the diameter of the circle of the mark 4b on the monitor may vary in conformity with the amount and direction of said rotation. By the rotative operation of the vertically movable ring 23, the examiner makes the diameter of the pupil and the diameter of the mark 4b coincident with each other on the monitor as shown in FIG. 15. When the measuring switch 21b is thereafter depressed, the value of D at this time is stored as the measured value of the diameter of the pupil. In a similar procedure, the present apparatus may be used as a cornea meter for measuring the diameter of the cornea of the eye to be examined.

The operation in a case where the present apparatus is an apparatus having the functions of observing the state of a cloud in the pupil of the eye to be examined and recording and redisplaying the image will now be described as still another embodiment of the present invention.

Figure 16:
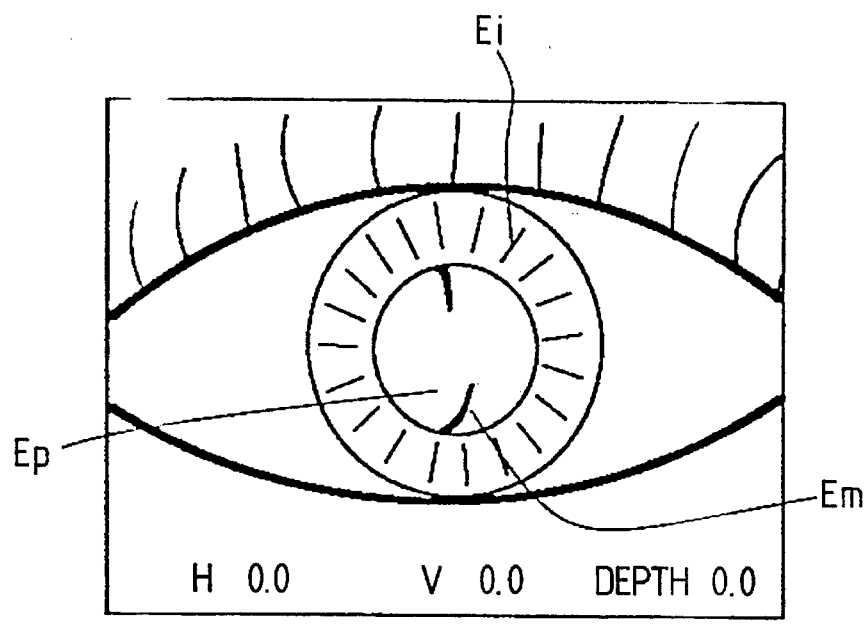
FIG. 16 illustrates the monitor display in an ophthalmologic apparatus according to still another embodiment of the present invention.
Figure 17:
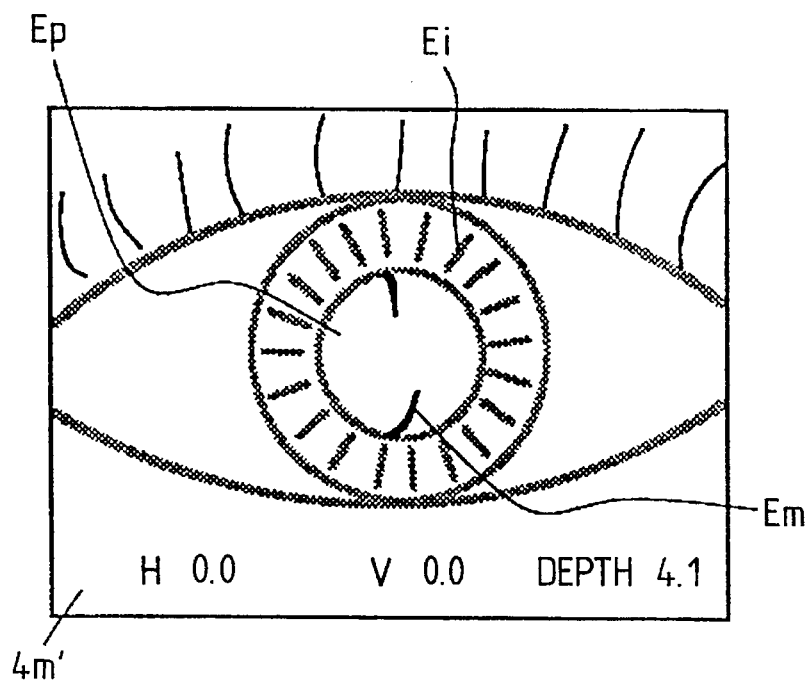
FIG. 17 illustrates the monitor display in the same apparatus.
Figure 18:
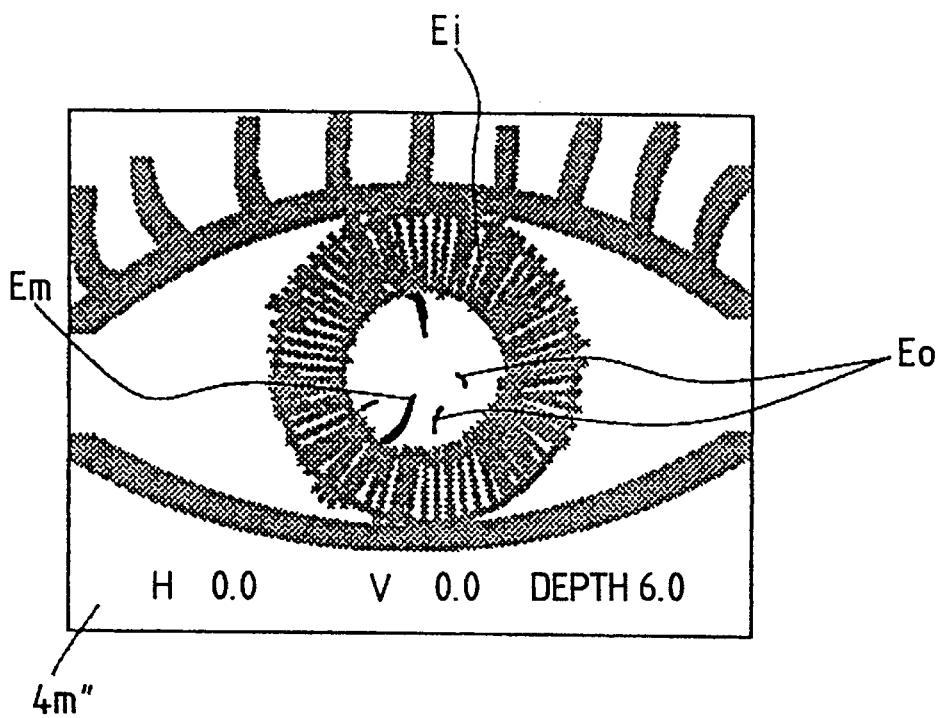
FIG. 18 illustrates the monitor display in the same apparatus.

FIG. 16 shows the monitor display in a state in which the apparatus is focused on the iris Ei of the eye E to be examined. When the measuring switch 21b is depressed at this time, positional data in that state is reset and as shown in FIG. 16, "H 0.0 V 0.0 depth 0.0" (H; horizontal V; vertical) is displayed on the lower portion of the monitor and at the same time, the image being displayed on the screen is stored in the frame memory 57. As the joy stick 21 is forwardly inclined from this state, the focus position moves from the iris Ei of the eye E to be examined to the crystalline lens portion and the then amount of movement is displayed as "depth 4.1" on the lower portion of the monitor as shown in FIG. 17. When the measuring switch 21b is again depressed in a state in which the apparatus is focused on the turbid portion Em, the image is stored in the frame memory 57. The monitor display, in a state in which the joy stick 21 is further forwardly inclined and the apparatus is focused on clouds in the vitreous body, is shown in FIG. 18. Eo designates clouds in the vitreous body. In this state, the measuring switch 21b is again depressed to thereby record the image. Respective image data have the relative moved position data of the slidable bed 2 also written therein and therefore, when the joy stick is moved forwardly and backwardly when a switch, not shown, is depressed to thereby redisplay the respective image data, an image is displayed on the monitor corresponding to the joy stick position in which the image has been recorded. Thus, at what location on the eye the displayed image has been picked-up can be seen at a glance.

Figure 19:
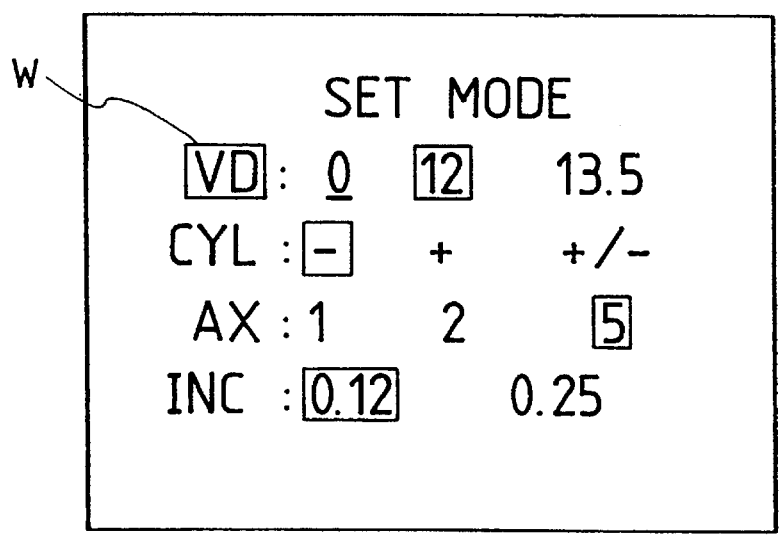
FIG. 19 illustrates the monitor display in an ophthalmologic apparatus according to yet still another embodiment of the present invention.
Figure 20:
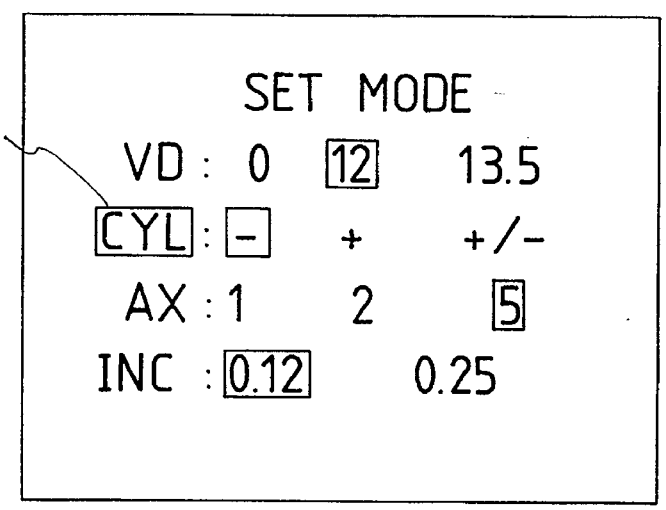
FIG. 20 illustrates the monitor display in the same apparatus.
Figure 21:
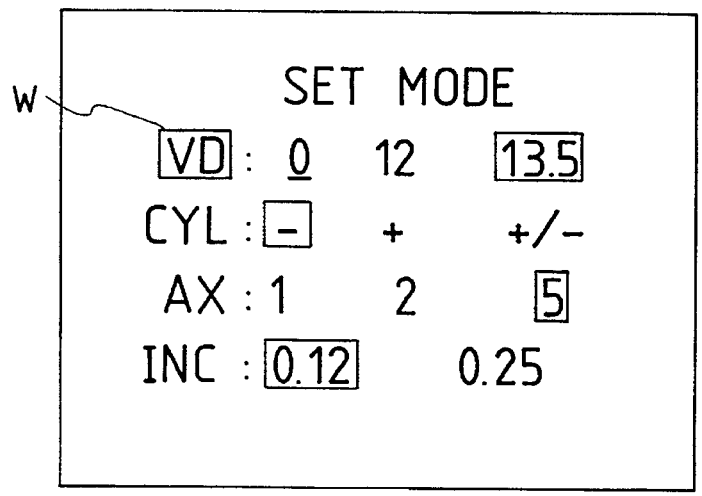
FIG. 21 illustrates the monitor display in the same apparatus.

FIGS. 19, 20 and 21 show monitor displays in still another embodiment in which, the present apparatus has the function of effecting the measurement of the refractive power of the eye. A set mode for effecting the setting when the measurement of the refraction of the eye is effected is illustrated in these figures. A description will hereinafter be provided with reference to these figures.

When a set switch, not shown, is depressed, the monitor 4 changes over to the set mode screen as shown in FIG. 19. In FIG. 19, "VD", "CYL", "AX" and "INC" represent set items, and they denote the distance between the vertices of the cornea, the astigmatism symbol, the rounded-off number when the angle of the astigmatic axis is displayed, and the rounded-off number when the degree of sphericity or the degree of astigmatism is displayed, respectively. A frame W is an item selecting cursor, and the position of the frame W moves up and down by the joy stick 21 being inclined forwardly and backwardly. FIG. 20 shows the monitor display when the joy stick 21 is inclined toward this side and "CYL" is selected. FIG. 21 shows the monitor display when from the state of FIG. 19, the joy stick 21 is inclined rightwardly. The position of the frame moves between the selection items of the set substances at the right of the "VD" display of the distance between the vertices of the cornea which is the selected item. In these figures, the set substance is changed from the selection item "12" to "13.5".

The joy stick may be a track ball.

As described above, according to each of the above-described embodiments, it has become possible to provide an ophthalmologic apparatus in which the switches are simplified and the simplification of operation is realized.

Particularly, the design of the device is such that the amount and direction of sliding movement by the input means for sliding movement are detected and image control can be effected on the basis of this detection, whereby the input means can be used as input means for image control without making any special improvement on the input means itself.

Also, the joy stick as the input means for sliding movement is used as input means for image control, whereby the operation for image control becomes easy without any special member being provided discretely.

Also the design of the device is such that the control for the disposition of the image of the eye to be examined displayed by the display means or the selection and designation of a particular one of a plurality of items displayed by the display means is effected on the basis of the input of the input means for sliding movement, whereby such control can be effected by a visually comprehensible operation.

Also, the input means for effecting vertical movement in addition to sliding movement can be used as input means for image control, whereby the kinds of the operations effected by this input means are increased.

What is claimed is:

1. An ophthalmologic apparatus comprising:
   a base;
   a slidable bed slidable on said base;
   input means for inputting instruction for sliding said slidable bed relative to said base from a user;
   display means for effecting image display of a stored instruction image; and
   control means for controlling an image display of the stored instruction image on said display means on the basis of an input effected by said input means by a technique similar to the input of instructions for sliding said slidable bed.

2. The apparatus according to claim 1, wherein said control means has detecting means for detecting the amount and direction of the sliding instructed by said input means, and image control means for effecting the control of the displayed image on said display means on the basis of the detection by said detecting means.

3. The apparatus according to claim 1, wherein said input means is a joy stick.

4. The apparatus according to claim 1, wherein said display means display a static image of an eye to be examined or a plurality of items of an eye to be examined, and said control means effects the control of the disposition of the static image of the eye to be examined which is displayed by said display means or the selection and designation of a particular one of the plurality of items displayed by said display means, on the basis of the input effected by said input means.

5. The apparatus according to claim 1, further comprising an optical unit carried on said slidable bed and vertically movable and wherein said input means effects inputting instructions for sliding said slidable bed relative to said base and for vertically moving said optical unit.

6. The apparatus according to claim 1, further comprising memory means for storing the stored image.

7. The apparatus according to claim 6, wherein said stored image is the image of an eye to be examined generated by an image pick-up device.

8. The apparatus according to claim 7, wherein by the input effected to said input means, a predetermined region of the picked-up image of the eye to be examined displayed on said display means can be moved to a position in which changeover to enlarged display of an image part thereof is possible on said display means.

9. The apparatus according to claim 7, wherein by the input effected by said input means, a predetermined region of the picked-up image of the eye to be examined which is displayed on said display means can be moved to a position on said display means for measuring the diameter of the pupil or the diameter of the cornea of the eye.

10. The apparatus according to claim 7, wherein corresponding to the input effected by said input means, a plurality of picked-up images of the eye to be examined differing in focus and stored in said memory means are displayed on said display means.

11. The apparatus according to claim 1, further comprising a unit provided on said slidable bed for measuring the eye to be examined and wherein said display means displays a plurality of items for the control of parameters during the measurement of the eye to be examined, and said control means effects the control of the selection and designation of a particular one of the plurality of items displayed by said display means, on the basis of the input effected by said input means.

12. An ophthalmologic apparatus comprising:

a base;

a slidable bed slidable on said base;

input means for inputting instructions for sliding said slidable bed relative to said base from a user;

a monitor for effecting instruction image display; and a processing circuit for controlling a displayed image on said monitor on the basis of an input effected by said input means by a technique substantially similar to the inputting of instructions for sliding by said input means, the displayed image to be controlled by said processing circuit not being a real-time image generated from an image pick-up device.

13. An ophthalmologic apparatus comprising:

a base;

a slidable bed slidable on said base;

input means for inputting instructions for sliding said slidable bed relative to said base from a user;

a monitor for effecting instruction image display; and a processing circuit for controlling a displayed image on said monitor on the basis of an input effected by said input means by a technique similar to the inputting of instructions for sliding, the displayed image to be controlled by said processing circuit being a freeze-frame image or a character image.

* * * * *

UNITED STATES PATENT AND TRADEMARK OFFICE
CERTIFICATE OF CORRECTION

PATENT NO. : 5,589,899  Page 1 of 3
DATED : December 31, 1996
INVENTOR(S) : YASUO MAEDA, ET AL.

It is certified that error appears in the above-indentified patent and that said Letters Patent is hereby corrected as shown below:

ON THE COVER PAGE:

[54] In The Title:

"OPTHALMOLOGIC" should read --OPHTHALMOLOGIC--.

COLUMN 1:

Line 1, "OPTHALMOLOGIC" should read --OPHTHALMOLOGIC--.

Line 16, "pickup" should read --pickup,--.

Line 49, "plate" should read --plate.--.

COLUMN 3:

Line 62, "Of the design" should read --of the device--.

UNITED STATES PATENT AND TRADEMARK OFFICE
CERTIFICATE OF CORRECTION

PATENT NO. : 5,589,899
DATED : December 31, 1996
INVENTOR(S) : YASUO MAEDA, ET AL.

It is certified that error appears in the above-indentified patent and that said Letters Patent is hereby corrected as shown below:

COLUMN 4:

Line 20, "devices" should read --device--.

COLUMN 5:

Line 10, "and" should read --are--.

UNITED STATES PATENT AND TRADEMARK OFFICE
CERTIFICATE OF CORRECTION

PATENT NO. : 5,589,899
DATED : December 31, 1996
INVENTOR(S) : YASUO MAEDA, ET AL.

It is certified that error appears in the above-indentified patent and that said Letters Patent is hereby corrected as shown below:

COLUMN 8:

Line 11, "instruction" should read --instructions--.

Line 30, "display" should read --displays--.

Signed and Sealed this

Twenty-fourth Day of June, 1997

Attest:

BRUCE LEHMAN

Attesting Officer     Commissioner of Patents and Trademarks